(12) United States Patent
Li

(10) Patent No.: US 11,879,972 B2
(45) Date of Patent: Jan. 23, 2024

(54) ULTRASONIC IMAGING APPARATUS AND METHOD, AND ULTRASONIC ELASTIC TESTING APPARATUS AND METHOD

(71) Applicants: SHENZHEN MINDRAY BIO-MEDICAL ELECTRONICS CO., LTD., Guangdong (CN); SHENZHEN MINDRAY SCIENTIFIC CO., LTD., Guangdong (CN)

(72) Inventor: Shuangshuang Li, Shenzhen (CN)

(73) Assignees: Shenzhen Mindray Bio-Medical Electronics Co., Ltd., Shenzhen (CN); Shenzhen Mindray Scientific Co., Ltd., Shenzhen (CN)

( * ) Notice: Subject to any disclaimer, the term of this patent is extended or adjusted under 35 U.S.C. 154(b) by 395 days.

(21) Appl. No.: 17/174,142

(22) Filed: Feb. 11, 2021

(65) Prior Publication Data
US 2021/0255320 A1 Aug. 19, 2021

Related U.S. Application Data

(63) Continuation of application No. PCT/CN2018/102319, filed on Aug. 24, 2018.

(51) Int. Cl.
*G01S 15/89* (2006.01)
*A61B 8/08* (2006.01)
(Continued)

(52) U.S. Cl.
CPC ........ *G01S 15/8906* (2013.01); *A61B 8/0858* (2013.01); *A61B 8/4483* (2013.01); *G01S 7/5202* (2013.01); *G01S 7/52085* (2013.01)

(58) Field of Classification Search
CPC . A61B 8/0858; A61B 8/4483; G01S 15/8906; G01S 7/5202; G01S 7/52085
See application file for complete search history.

(56) References Cited

U.S. PATENT DOCUMENTS 5,991,239 A * 11/1999 Fatemi-Booshehri ...................... G10K 15/02
367/164
7,785,259 B2 * 8/2010 Zheng .................... A61B 8/485
600/444

(Continued)

FOREIGN PATENT DOCUMENTS

| CN | 1990063 A | 7/2007 |
| CN | 102809610 A | 12/2012 |
| CN | 103260527 A | 8/2013 |

OTHER PUBLICATIONS

PCT International Search Report and the Written Opinion dated Dec. 6, 2018, issued in related International Application No. PCT/CN2018/102319, with partial English translation (8 pages).

*Primary Examiner* — Dixomara Vargas
(74) *Attorney, Agent, or Firm* — Sheppard Mullin Richter & Hampton LLP

(57) ABSTRACT

A method and apparatus for generating a shear wave. The method comprises: transducers transmit ultrasound waves to a region of interest once; the ultrasound waves focus on at least two focal points in an acoustic field; and with shear wave sources corresponding to the at least two focal points that propagates in a direction perpendicular to a transmission direction of the ultrasound waves. A method and apparatus for detecting an ultrasound elasticity of a shear wave discloses, in a same ultrasound transmission, multiple focal points are gathered in an acoustic field by the ultrasound waves, under the joint effect of the multiple focal points, and a shear wave zone propagated in a direction perpendicular to (Continued)

a direction in which the ultrasound waves is transmitted is formed, so as to expand a propagation range of the shear wave in a tissue, so that detecting ultrasound waves can perform elasticity detection on the tissue in a large range.

17 Claims, 6 Drawing Sheets

(51) Int. Cl.
    *A61B 8/00*     (2006.01)
    *G01S 7/52*     (2006.01)

(56) References Cited

U.S. PATENT DOCUMENTS

| | | | |
|---|---|---|---|
| 10,231,712 B2* | 3/2019 | Ebbini | G16H 50/30 |
| 10,448,924 B2 | 10/2019 | Fraser et al. | |
| 10,959,704 B2* | 3/2021 | Kanayama | G01S 7/52022 |
| 2007/0038095 A1* | 2/2007 | Greenleaf | A61B 8/485 |
| | | | 600/438 |
| 2011/0319756 A1* | 12/2011 | Zheng | G01S 7/52022 |
| | | | 600/438 |
| 2012/0116220 A1* | 5/2012 | Burcher | A61B 8/00 |
| | | | 600/438 |
| 2013/0317361 A1* | 11/2013 | Tabaru | G01S 7/52042 |
| | | | 600/438 |
| 2013/0317362 A1* | 11/2013 | Shi | A61B 8/5207 |
| | | | 600/438 |
| 2014/0005548 A1* | 1/2014 | Fraser | A61B 8/5276 |
| | | | 600/447 |
| 2018/0214135 A1* | 8/2018 | Yamamoto | A61B 8/14 |
| 2019/0328364 A1* | 10/2019 | Questa | G01S 7/52042 |
| 2019/0350559 A1* | 11/2019 | Bini | A61B 8/485 |
| 2020/0060653 A1* | 2/2020 | Kong | A61B 8/463 |
| 2020/0077977 A1* | 3/2020 | Tsushima | G01N 29/0645 |
| 2020/0187909 A1* | 6/2020 | Yoshikawa | A61B 8/0858 |
| 2020/0268356 A1* | 8/2020 | Li | A61B 8/085 |
| 2020/0297319 A1* | 9/2020 | Kong | A61B 8/58 |
| 2020/0337679 A1* | 10/2020 | Watanabe | A61B 8/485 |
| 2021/0007712 A1* | 1/2021 | Fuse | G01S 7/52022 |
| 2021/0022710 A1* | 1/2021 | Crocco | G01S 15/8915 |
| 2022/0104794 A1* | 4/2022 | De Beni | G06N 20/00 |

\* cited by examiner

ULTRASONIC IMAGING APPARATUS AND METHOD, AND ULTRASONIC ELASTIC TESTING APPARATUS AND METHOD

This application is a continuation application of International Patent Application No. PCT/CN2018/102319, filed with the China National Intellectual Property Administration (CNIPA) on Aug. 24, 2018. The content of the above application is incorporated herein by reference in its entirety.

TECHNICAL FIELD

The present disclosure relates to ultrasonic devices.

BACKGROUND OF THE INVENTION

Ultrasound elasticity imaging mainly presents the elasticity or hardness of tissues, and it has been used more and more in the auxiliary detection, discrimination of benign and malignant and evaluation of prognosis recovery, etc. of a tissue cancer lesions.

Ultrasound shear wave elasticity imaging is one of the ultrasound elasticity imaging methods which detects the hardness of a tissue. In the ultrasound shear wave elasticity imaging, a propagation of the shear wave in the tissue may be detected to obtain its propagation parameters (e.g. propagation velocity), and for an isotropic elastic tissue, there is a following relationship between the propagation velocity of the shear wave and elastic modulus of the tissue: Young's modulus $E=3\rho Cs^2$. Thus, It is clear that there is a one-to-one correspondence between a shear wave velocity and the elastic modulus, so a difference in hardness between the tissues can be represented in accordance with the shear wave velocity. Such the method can make it more convenient and objective for doctors to diagnose due to its quantitative hardness measurement results, so it has been widely concerned and welcomed by doctors.

There are two main methods for generating a shear wave in the tissue. One is to generate the shear wave which propagates into the tissue through external vibration. The other is to use ultrasound acoustic radiation force to transmit an ultrasound waves with a specific length into the tissue to generate the shear wave which propagate in a direction perpendicular to the transmission direction. Since the shear wave generated by the method based on acoustic radiation force is relatively weak, it is often necessary to set a specific focus position to generate a relatively strong shear wave source on a focal point so as to increase the amplitude of the shear wave. However, this also leads to a smaller propagation range of the shear wave, obtaining only a very limited range of elasticity results.

SUMMARY OF THE INVENTION

A technical problem mainly solved by the present disclosure is how to expand the propagation range of a shear wave.

According to a first aspect, a method for generating a shear wave provided in one embodiment may include:

transmitting ultrasound waves to a region of interest through transducers in an ultrasound probe that are configured to transmit ultrasound waves;

the ultrasound waves focus on at least two focal points in an acoustic field; and the ultrasound waves drive a tissue so as to form a shear wave zone with shear wave sources corresponding to the at least two focal points, wherein the shear wave zone is propagated in a direction perpendicular to a transmission direction of the ultrasound waves.

According to a second aspect, a method for detecting an elasticity with a shear wave disclosed in one embodiment may include:

transmitting ultrasound waves to a region of interest through transducers in an ultrasound probe that are configured to transmit ultrasound waves, wherein the ultrasound waves are focused on at least two focal points in an acoustic field and drive a tissue so as to form a shear wave zone with shear wave sources corresponding to the at least two focal points, wherein the shear wave zone is propagated in a direction perpendicular to a transmission direction of the ultrasound waves;

continuously transmitting detection ultrasound waves for a predetermined duration to a propagation path of the shear wave zone through transducers configured to transmit detection ultrasound waves, and receiving echo signals of the detection ultrasound waves; and calculating elastic characteristic values based on the echo signals.

According to a third aspect, an method for an ultrasound imaging method disclosed in one embodiment may include:

determining at least two focal points in a region of interest in a biological tissue along a direction in which ultrasound waves are transmitted;

outputting transmission parameters to transducers disposed in an ultrasound probe and configured to transmit the ultrasound waves, so as to divide the transducers into at least two groups, each group corresponding to a focal point;

transmitting ultrasound waves into the tissue through the transducers of each group according to the transmission parameter, so that the ultrasound waves are focused on the focal point corresponding to the group;

receiving echo signals of the ultrasound waves; and generating an ultrasound image according to the echo signals.

According to a fourth aspect, an ultrasound elasticity detecting apparatus provided in one embodiment may include an ultrasound probe, a transmitting/receiving controller and a data processor.

The ultrasound probe comprising a plurality of transducers configured to transmit ultrasound waves, the transducers being at least configured to transmit ultrasound waves to a region of interest, the ultrasound waves being focused on at least two focal points in an acoustic field, the ultrasound waves driving a tissue so as to form a shear wave zone with shear wave sources corresponding to the at least two focal points, the shear wave zone being propagated in a direction perpendicular to a transmission direction of the ultrasound waves, and the ultrasound probe being further configured to continuously transmit detection ultrasound waves for a predetermined duration to a propagation path of the shear wave zone and receive echoes of the detection ultrasound waves; the transmitting/receiving controller being configured to generate transmission parameters and output the transmission parameters to the ultrasound probe, the transmission parameters comprising parameters of the ultrasound waves or parameters of the detection ultrasound waves; and the data processor being configured to calculate an elastic characteristic value based on the echoes of the detection ultrasound waves.

According to a fifth aspect, an ultrasound imaging apparatus provided in one embodiment may include an ultrasound probe, a transmitting/receiving controller being configured to determine at least two focal points in a region of interest of a biological tissue along a direction in which ultrasound waves are transmitted, the transmitting/receiving controller being further configured to generate a transmission parameter based on the at least two focal points and output the transmission parameter to the ultrasound probe; the ultrasound probe comprising a plurality of transducers arranged in an array, the ultrasound probe being configured to transmit ultrasound waves to the region of interest of the biological tissue based on the transmission parameter and receive echoes of the ultrasound waves, the transducers configured to transmit the ultrasonic waves and being divided into at least two groups according to the transmission parameter, and the ultrasound waves transmitted by each group being focused on a focal point; and the data processor being configured to generate an ultrasound image based on the echoes.

According to a sixth aspect, a computer-readable storage medium provided in one embodiment may include a program which is executable by a computer to implement the above method.

In the embodiments of the present disclosure, since ultrasound waves in a same transmission are converged into a plurality of focal points, a shear wave zone propagated in a direction perpendicular to a direction in which the ultrasound waves are transmitted is formed under the joint action of the plurality of focal points, expanding the range of the shear wave propagating in a tissue, and in this respect elastic measuring on the tissue in a large range can be performed by the detection ultrasound waves.

DETAILED DESCRIPTION

The present disclosure will be described in detail below with reference to the embodiments and drawings, wherein similar elements in different embodiments are designated with similar reference numbers. In the following embodiments, many details are described so as to facilitate the understanding to the present disclosure. However, those skilled in the art will easily recognize that some of the features may be omitted in different situations, or may be replaced by other elements, materials or methods. In some cases, some operations are not shown or described in the specification, which is to avoid the core part of the present disclosure being overwhelmed by too many descriptions. For those skilled in the art, detailed description of these operations is not necessary. They can fully understand these operations according to the description in the specification and general technical knowledge in the field.

In addition, the features, operations or characteristics described in the specification may be combined in any appropriate manner to form various embodiments. Furthermore, the steps or actions in the described methods may also be changed or adjusted in the order in a manner obvious to those skilled in the art. Therefore, the various orders in the description and drawings are only for clearly describing a certain embodiment, but not meant to be a necessary order unless otherwise stated that a certain order must be followed.

The serial numbers for the elements in the present disclosure, such as "first", "second", etc., are only used to distinguish the described objects, but do not have any order or technical meaning. The "connection" and "coupling" as used herein, unless otherwise specified, will include both direct and indirect connection (coupling).

In the case of the shear wave generated by using the acoustic radiation force of ultrasound waves, during a same transmission of the ultrasound waves, at least two focal points are selected along a transmission direction in which the ultrasound waves are transmitted in the embodiments of the present disclosure, the transducers used for transmitting are divided into at least two groups, and the ultrasound waves are focused on the focal points to finally form a strong and uniform segment of linear acoustic-field zone in the transmission direction, thereby generating shear wave propagated at both sides within the depth range of the acoustic-field zone, expanding the generation and propagation range of shear wave.

Figure 1:
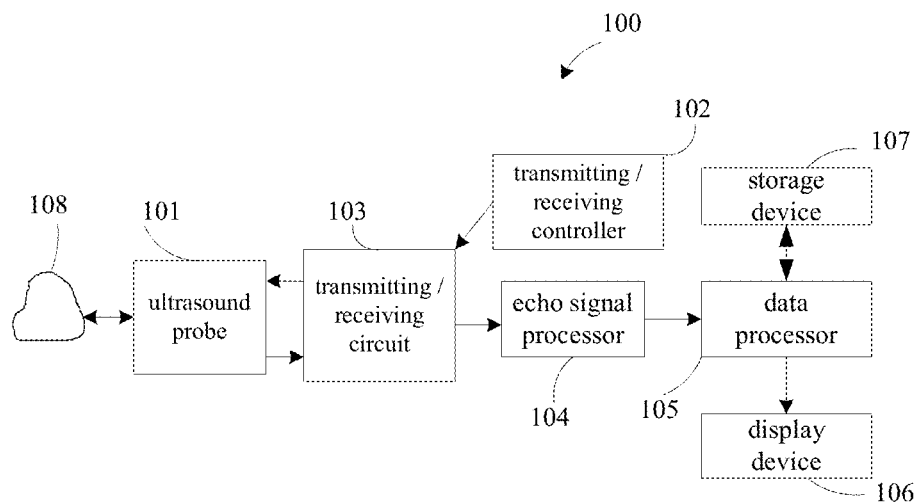
FIG. 1 is a schematic structural diagram of an ultrasound elasticity imaging apparatus according to one embodiment.

Referring to FIG. 1, the structure of an ultrasound elasticity imaging apparatus 100 may, as shown in FIG. 1, include an ultrasound probe 101, a transmitting/receiving controller 102, a data processor 105, a display device 106 and a storage device 107. In a specific example, the ultrasound elasticity imaging apparatus 100 may further include a transmitting/receiving circuit 103 and an echo signal processor 104. In this example, the transmitting/receiving controller 102 is connected to the ultrasound probe 101 through the transmitting/receiving circuit 103, the ultrasound probe 101 is connected to the echo signal processor 104 through the transmitting/receiving circuit 103, the output of the echo signal processor 104 is connected to the data processor 105, and the output of the data processor 105 is connected to the display device 106. The storage device 107 is connected to the data processor 105.

The ultrasound probe 101 may be configured to convert an electric pulse signal with an ultrasound wave in a mutual way, so as to transmit the ultrasound wave to a measured biological tissue 108 (such as biological tissues of a human or animal body) and receive ultrasound echo reflected by the tissue. The ultrasound probe 101 in the embodiment may include a plurality of transducers (also referred to as ultrasonic transducers) arranged in a row to form a linear array, or in a two-dimensional matrix to form an area array, or in a convex array. The transducers may be configured to transmit ultrasound waves based on an electrical excitation signal, or to convert the received ultrasound waves into electrical signals. Therefore, each transducer can be used to transmit ultrasound waves to the region of interest of a biological tissue, and can also be used to receive echoes of the ultrasound waves through the tissue. A transmitting sequence and a receiving sequence are adopted during ultrasound testing to control which transducers are used to transmit and which to receive ultrasound waves, or to control the transducers to transmit ultrasound waves or receive the echoes in different times. All transducers configured to transmit ultrasound waves can be excited by electrical signals simultaneously, thereby transmitting ultrasound waves at the same time; or the transducers configured to transmit ultrasound waves can be excited by several electrical signals with a certain time interval, so as to continuously transmit ultrasound waves with a certain time interval. Multiple adjacent transducers are usually formed as a group of transducers to perform transmitting or receiving simultaneously to increase working aperture in practical applications.

Figure 2:
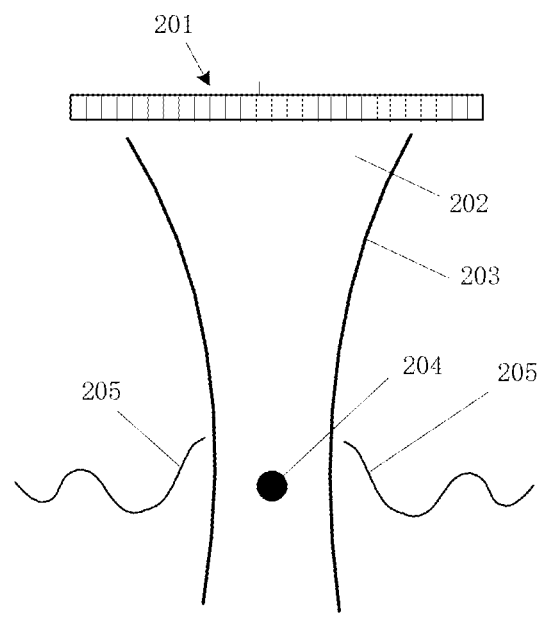
FIG. 2 is a schematic diagram showing a focus of ultrasound waves emitted by transducers.

The transmitting/receiving controller 102 may be configured to generate the transmitting sequences and output the transmitting sequences to the ultrasound probe. The transmitting sequences may be used to control part or all of the multiple transducers to transmit ultrasound waves to the biological tissue of the region of interest. The transmitting sequences may also provide transmission parameters, including the amplitude, frequency, number of transmitting, transmitting angle, wave type and/or focus position of the ultrasound waves. The transmission parameters can be adjusted to control the wave type, the transmission direction and focus position of the transmitted ultrasound waves according to different applications. The wave type of ultrasound waves may be ultrasound waves, plane waves, etc. When a shear wave needs to be generated, the transmitting/receiving controller 102 usually controls several adjacent transducers to transmit ultrasound waves through the transmission parameters. As shown in FIG. 2, the ultrasound waves 202 transmitted by each transducer 201 may be spatially superimposed to synthesize ultrasound beams which will be converged to focus on a focal point 204. An acoustic field 203, formed by the synthetic ultrasound beams, may refer to space covered or passed by the synthetic ultrasound beams. It may be an energy distribution field in the space after each time of ultrasound transmission, in which the energy is not uniformly distributed, generally the closest to the focus position the highest the energy and the farther away from the focus position the lowest the energy. When the energy is attenuated relative to the maximum energy to be a certain extent, the boundary of the acoustic field may be formed at the left and right positions as shown. A specific acoustic field range and focus position may be formed by the transmitted ultrasound waves controlled by transmission parameters. A momentary downward force may be produced at the focal point 204 on the tissue by ultrasound waves 202. When the force disappears, the shear wave 205 may be generated in the tissue and propagated to both sides centered on focal point 204 due to the elasticity of the adhesion between tissues and the elasticity of the tissues. The focal point 204 is therefore also referred to as a shear wave source, and the propagation direction of the shear wave 205 is perpendicular to the direction of the ultrasound beams. When the shear wave may need to be detected, the transmitting/receiving controller 102 may control several adjacent transducers to transmit ultrasound waves for a period of time on the propagation path of the shear wave through transmission parameters; and meanwhile the transmitting/receiving controller 102 may control transducers configured for receiving to receive the echo of ultrasound waves. The shear wave generated in this way can only be propagated within a small area, and can only be used to detect the elastic characteristic values of the tissues within a small area.

The transmitting/receiving circuit 103 connected between the ultrasound probe and the transmitting/receiving controller 102 and the echo signal processor 104 is configured to transmit the transmitting sequence of the transmitting/receiving controller 102 to the ultrasound probe 101, and to transmit the ultrasound echo signals received by the ultrasound probe 101 to the echo signal processor 104.

The echo signal processor 104 may be configured to process the ultrasound echo signals, including filtering, amplifying, beam forming and other processing on the ultrasound echo signals, to obtain ultrasound echo data. In a specific embodiment, the echo signal processor 104 may be configured to output ultrasound echo data to the data processor 105; alternately, the ultrasound echo data may first be stored in the storage device 107, and then be read out from the storage device 107 from the data processor 105 when calculation(s) based on the ultrasonic echo data are required.

The storage device 107 may be configured to store data and programs. The programs may include system programs of an ultrasound device, various application programs, or algorithms for implementing various specific functions.

The data processor 105 may be configured to obtain the ultrasound echo data, and use related algorithms to gain required parameter(s) or image(s). For example, the data processor 105 may generate an ultrasound image based on the ultrasound echo data, or generate an elastic image based on the ultrasound echo data.

In an embodiment, the transducers configured to transmit ultrasound waves may be divided into at least two groups. For example, there are N transducers used to transmit ultrasound waves, adjacent N1 transducers form a first group, and adjacent N2 transducers form a second group, . . . , and adjacent Nn transducers form an nth group, wherein N1, N2, . . . , Nn are positive integers, and N1+N2+ . . . +Nn=N. one group of transducers may be corresponded to one focal point by configuring the transmission parameters, for example, configuring the emission angle and focus position of the transmission parameters. When adjacent N transducers transmit the ultrasound waves, synthetic ultrasound beams may be formed by converging the ultrasound waves transmitted by the N transducers due to the action of an acoustic lens. Since different groups of transducers correspond to different focus positions, n focal points may be formed in the acoustic field. Each focal point may form a shear wave source, generating a shear wave that propagates in a direction perpendicular to the transmission direction of the ultrasound waves. Thus n focal points form n shear wave source that are propagated in a direction perpendicular to the transmission direction of the ultrasound waves, forming a shear wave zone so as to expand the propagation range of shear wave. By controlling the focus position, the distance between adjacent focal points can be adjusted. And when adjacent shear wave sources are close enough, they may be influenced each other, increasing the vibration amplitude of the shear wave sources, thereby enhancing the amplitude of the shear wave, decreasing the influence of interference on the shear wave and improving the signal-to-noise ratio of the detection.

In a preferred embodiment, the transmitting/receiving controller 102 may also perform a delay processing according to a distance from the transducer(s) to the focal point(s) when outputting control signal(s) to the ultrasound probe, such that the ultrasound waves transmitted through each transducer in the same group can arrive at the focus position corresponding to the group at the same time. With ultrasound waves transmitted by each transducer arriving simultaneously at the focus position, the intensity of ultrasound waves at the focus position can be maximized, so is the amplitude of the shear wave source formed at the focus position. In a further improved embodiment, the ultrasound waves transmitted from all groups of transducers may also arrive at corresponding focus positions of each group at the same time, so that the various shear wave sources may be vibrated synchronously to make adjacent shear wave sources influence each other in the same direction, helping to increase the amplitude of the shear wave.

For each group of transducers, different transducers therein have relative transmission delays according to the distance from each transducer to the focal point corresponding to the group, so that the ultrasound waves emitted by different transducers in the group arrive at the focal point corresponding to the group simultaneously.

Figure 3:
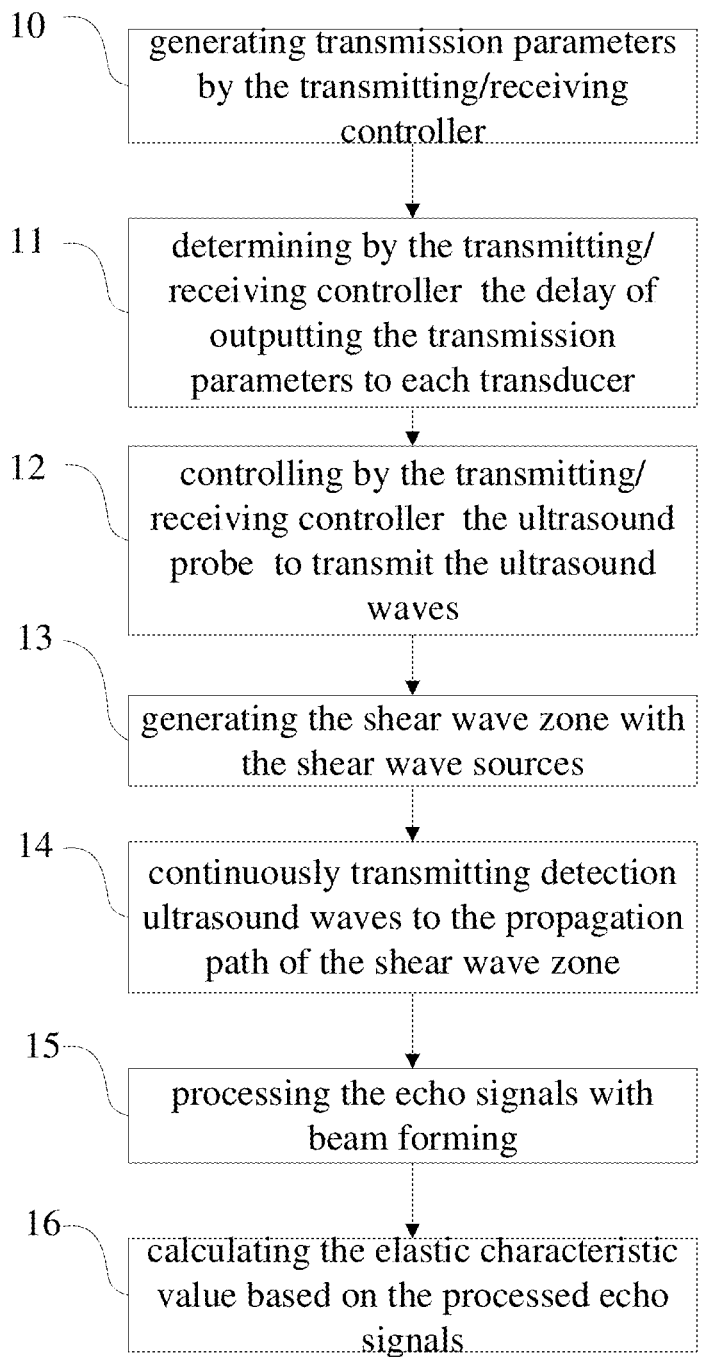
FIG. 3 is a flowchart of generating and detecting a shear wave according to one embodiment.

The generation and detection of the shear wave may be illustrated by taking the generation of three focal points as an example as follows. It may include the following steps as shown in FIG. 3.

Step 10: generating transmission parameters by the transmitting/receiving controller 102.

The transmission parameters may include the amplitude of ultrasound waves, a number of transmitting, transmitting angle, focus position and other parameters.

Figure 4:
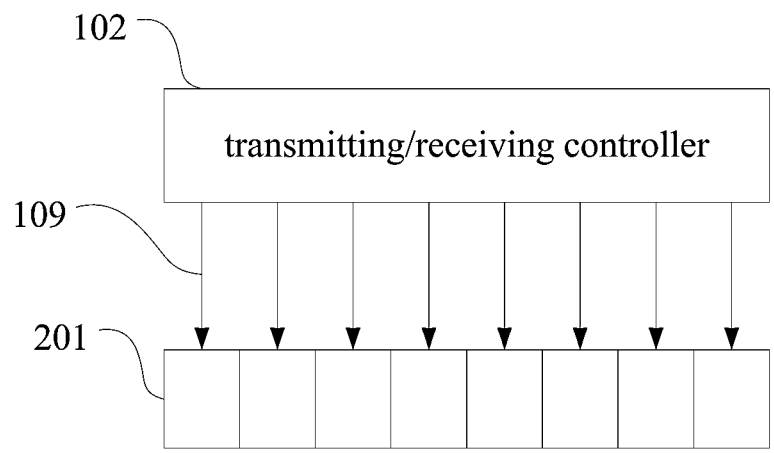
FIG. 4 is a schematic diagram of a connection between the transmitting/receiving controller and the transducers.

Regarding to focus position, firstly, the number of focal points may be determined. The number of focal points may be preset, or be determined with a value entered by a user in a dialog window. When the number of focal points is determined, for example the number of focal points is three, the transmitting/receiving controller 102 may determine three focus positions according to the number of focal points and the position of the region of interest, assign transducers to each focal point, and output the transmission parameters to a corresponding transducer. The determined focus position may be usually located at the focus position of the synthetic ultrasound beams. As shown in FIG. 4, the transmitting/receiving controller 102 may output the transmission parameters to multiple transducers 201 through connecting lines 109. The corresponding relationship between focus positions of the output transmission parameters and the transducers is shown in Table 1 as below.

TABLE 1

| transducer | focus position | transducer group |
|---|---|---|
| transducer 1 | focus position 1 | group 1 |
| transducer 2 | focus position 1 | |
| transducer 3 | focus position 1 | |
| transducer 4 | focus position 2 | group 2 |
| transducer 5 | focus position 2 | |
| transducer 6 | focus position 2 | |
| transducer 7 | focus position 3 | group 3 |
| transducer 8 | focus position 3 | |
| transducer 9 | focus position 3 | |

It can be seen from the above table that the transducers that receive the same parameter about the focus position may be regarded as falling in the same group. The number of transducers in each group may be the same or different.

In an improved embodiment, the transmitting/receiving controller 102 may, according to focus depth and focus strength, determine suitable probe transducers for transmitting, such as the position of the transducers and the number of the transducers. When the focus position is determined, the number of transducers in each transducer group may affect the focus strength which may be judged by an index Fnumber. Fnumber directly affects the shape of the acoustic field and the width of the boundary of the acoustic field. The relationship between the number of transducers in each transducer group and Fnumber is as follows:

$$Fnumber = focus\ depth / transmitting\ aperture \quad (1)$$

where Fnumber is a characteristic value that represents a focus strength, the focus depth is a distance from the focal point to the surface of the tissue(s), and the transmitting aperture is a maximum width range formed by all the transducers that transmit the ultrasound waves focused on the focal point. The width of the transducers configured for transmitting is also the transmitting aperture, and the width of the transducers is proportional to the number of transducers.

When Fnumber grows larger, it means that the focus strength becomes weaker and the acoustic field of the converging part gets more dispersed with its increasing width; and while Fnumber goes smaller, it represents that the focus strength gets stronger and the acoustic field of the converging part becomes more concentrated with its narrowing width.

It can be seen from formula (1) that when the focus position is determined, the number of transducers in each transducer group may be determined according to a required Fnumber.

Step 11: determining by the transmitting/receiving controller 102 the delay of outputting the transmission parameters to each transducer.

The times of the ultrasound waves transmitted by each transducer arriving at respective corresponding focus position are different, due to different distances from each transducer to its corresponding focus position. To make the ultrasound waves transmitted by each transducer simultaneously arrive at respective corresponding focus position, some transducers may be controlled to delay the transmission of ultrasonic waves. The transmitting/receiving controller 102 may acquire the distance from an transducer to its corresponding focus position based on the transducer and the focus position, and calculate out the time the ultrasound waves arrived at the focus position according to the distance and the propagation velocity of the ultrasound waves in the tissues, thus, to determine the delay of the transducer transmitting ultrasound waves.

Step 12: controlling by the transmitting/receiving controller 102 the ultrasound probe 101 to transmit the ultrasound waves.

Figure 5:
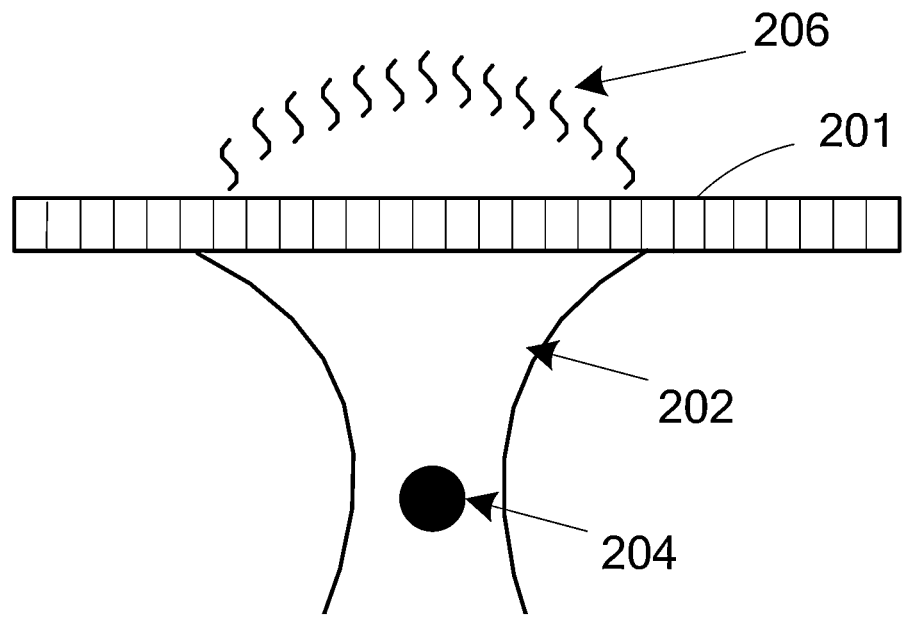
FIG. 5 is a schematic diagram showing an transmission parameter outputting to the transducers in a delayed manner.
Figure 6:
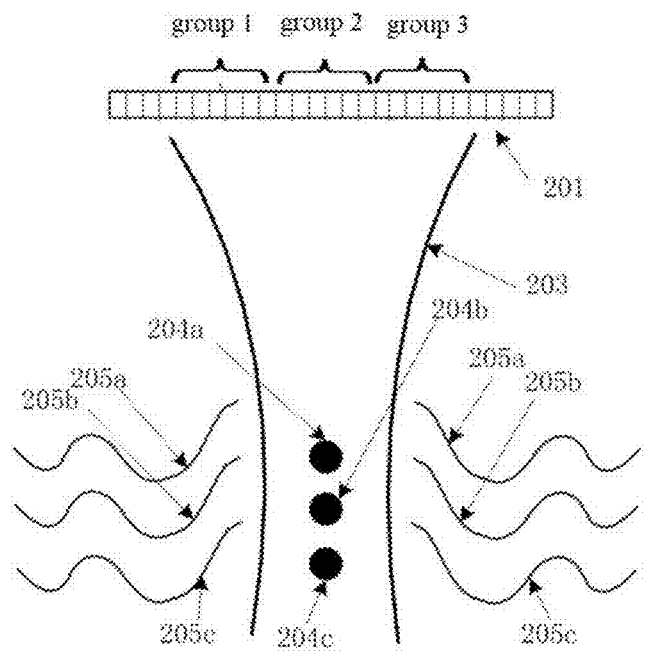
FIG. 6 is a schematic diagram showing a shear wave generated by multiple focal points.

The transmitting/receiving controller 102 may transmit transmission parameters 206 after a delay to each transducer 201. As shown in FIG. 5, after receiving the transmission parameters 206 the transducer 201 may transmit the ultrasound waves 202 based on the transmission parameters 206, and the ultrasound waves may arrive at respective focus positions (i.e. focal points) 204 at the same time. For example, the ultrasound waves transmitted by the transducers in group 1 are focused on a first focal point 204a, the ultrasound waves transmitted by the transducers in group 2 are focused on a second focal point 204b, and the ultrasound waves transmitted by the transducers in group 3 are focused on a third focal point 204c, as shown in FIG. 6.

After the above-mentioned processing, the ultrasound probe can make the ultrasound waves be focused synchronously on the corresponding focus position of each transducer group by the transmission of ultrasound waves for one time.

Step 13: generating the shear wave zone with the shear wave sources.

Figure 7:
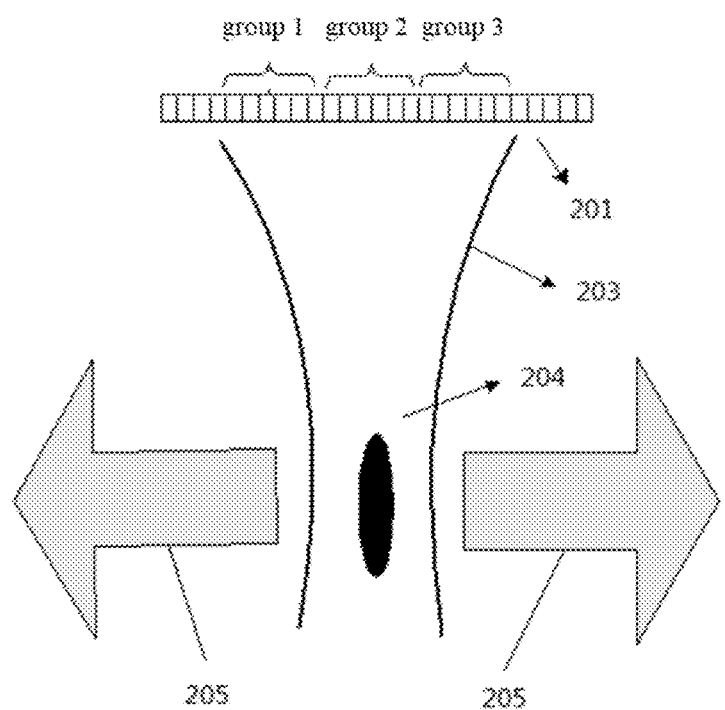
FIG. 7 is a schematic diagram showing a shear wave generated by a combined shear wave source.

In the embodiment, three focal points may form three shear wave sources, with the first focal point 204a forming a first shear wave 205a, the second focal point 204b forming a second shear wave 205b, and the third focal point 204c forming a third shear wave 205c. The three shear waves may respectively be propagated in a direction perpendicular to the transmission direction of the ultrasound waves, thereby forming a shear wave zone. By controlling the positions of the focal points, when the three focal points are physically adjacent and vibrated synchronously in the same direction, the shear wave sources of the three focal points can be interacted and the three focal points may connected together to form a shear wave source having a range similar to a straight line, as shown in FIG. 7. After this combined shear wave source is generated, the energy is the strongest and the amplitude is the largest in this area, and a shear wave zone 205 propagating to both sides is produced within an extended depth range.

Step 14: continuously transmitting detection ultrasound waves to the propagation path of the shear wave zone.

The transmitting/receiving controller 102 outputs the transmission parameters to the transducers configured to transmit the detection ultrasound waves. The transmission parameters may include ultrasound wave type, emission frequency, emission angle, emission duration, and amplitude. The transducers continuously transmit detection ultrasound waves with the predetermined duration to the propagation path of the shear wave zone based on the transmission parameters, and the transducers configured to receive the echoes of the detection ultrasound waves.

In this embodiment, since a shear wave zone propagating in the tissue is formed in the region of interest, every position within the range of propagation path of the shear wave can be detected.

Step 15: processing the echo signals with beam forming.

Step 16: calculating the elastic characteristic values based on the processed echo signals.

A displacement may occur on the tissues located on the propagation path of the shear wave zone due to the action of the shear wave. The data processor can determine the displacement of the tissue during the travel of the shear wave according to the ultrasound echo data of two frames generated before and after the tissue displacement. By deriving the displacement with respect to time, the propagation velocity of the shear wave in the tissue can be calculated $C_s$. There is the following relationship between the propagation velocity $C_s$ of the shear wave and the elastic modulus E of the tissue:

$$E = 3\rho C_s^2$$

wherein $\rho$ represents the density of the tissue. In other words, there is a one-to-one correspondence between the shear wave velocity and the elastic modulus, and the hardness of tissues can be represented by the shear wave velocity.

By means of forming a plurality of focal points in the acoustic field, the shear wave zone propagated in the region of interest can therefore be generated, thus, expanding the range of the shear wave propagated in the tissue, so that the detection ultrasound waves can perform elastic measuring on the tissue in a large range in this embodiment. Compared to those technical solutions adopting transmission of ultrasound waves as well as detection ultrasound waves for a plurality of times, the scheme in this embodiment can perform elastic measuring on the tissues in a large range by transmitting ultrasound waves and detection ultrasound waves for one time, thereby enhancing the detection speed and the comfort of a person to be detected.

Figure 8A:
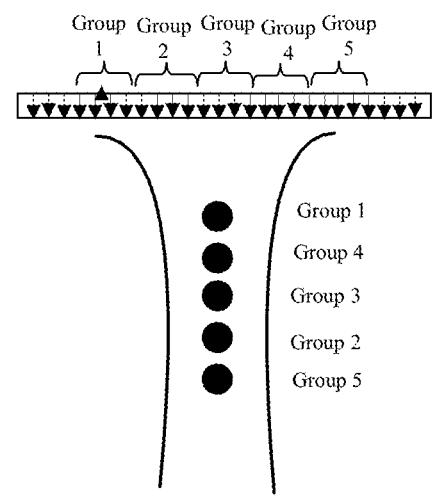
FIG. 8*a* is a schematic diagram showing a shear wave generated by five focal points.
Figure 8B:
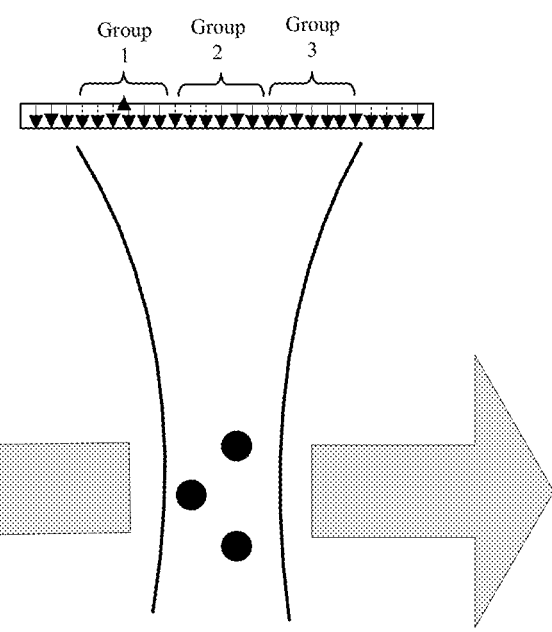
FIG. 8*b* is a schematic diagram showing a shear wave generated by multiple focal points distributed on a curve.
Figure 8C:
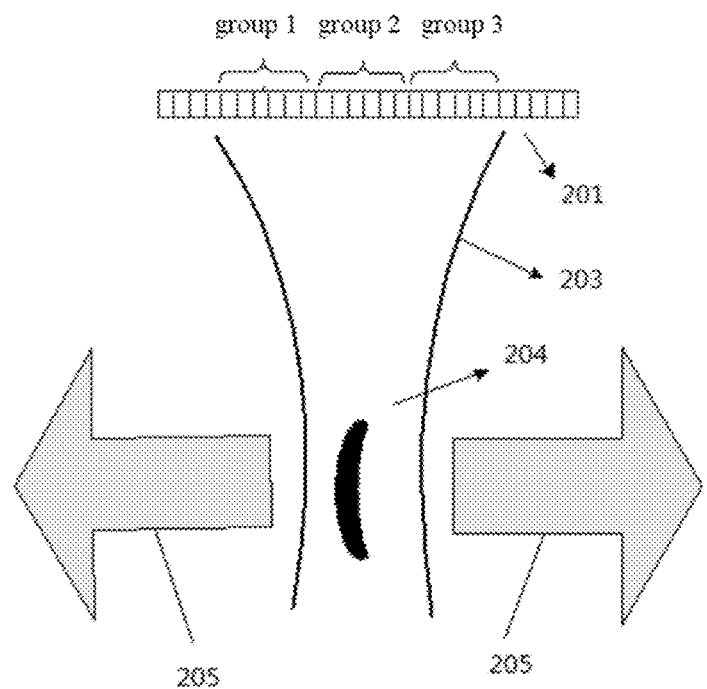
FIG. 8*c* is a schematic diagram showing a shear wave generated by a curved combined shear wave source.
Figure 8D:
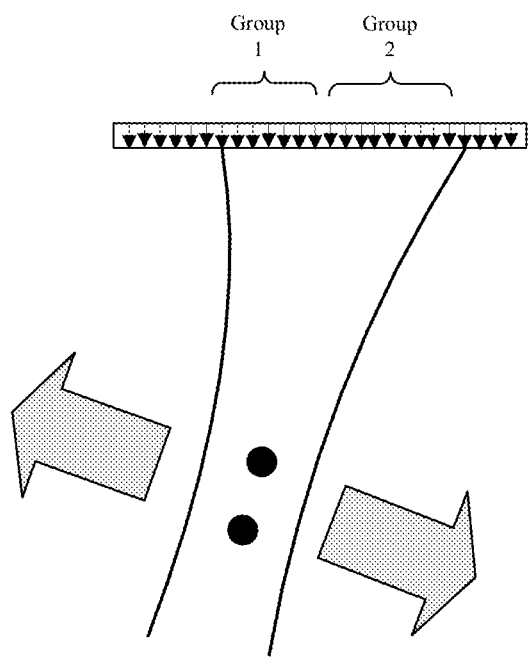
FIG. 8*d* is a schematic diagram of multiple focal points generated by ultrasound waves with a certain deflection angle.

Three focal points are used as examples for description in this embodiment, however there may be two, four or five focal points in other embodiments. As shown in FIG. 8a, the transducers are divided into five groups, which are focused on the five focal points in the acoustic field. The plurality of focal points in the acoustic field are distributed on a straight line in this embodiment, and they also can be distributed on a curve in the acoustic field in other embodiments as shown in FIG. 8b, or they can be distributed on other shapes or irregularly in the acoustic field, finally producing the combined shear wave source which may be as shown FIG. 8c. Moreover, the positions of the focal points are not required to be always in a direction perpendicular to the probe in the disclosure, that is, the direction of the synthetic ultrasound beams is not needed to be vertical to the probe. As shown in FIG. 8d, the direction of the synthetic ultrasound beams may also be deflected at an angle with respect to the normal of the probe, and the resulted effect thereof is similar to that of transmission deflected at a certain angle under the above-mentioned arrangement of vertical emission.

The solution of the present disclosure may also be applicable to ultrasonic transducers arranged in different shapes, such as linear arrangement, convex arrangement, circular arrangement, etc.

The solution of the present disclosure is not limited to being applied to shear wave imaging, but also applicable to other imaging methods. For example, during performing B imaging, the transducers configured to transmit ultrasound waves may be divided into at least two groups by the setting(s) of ultrasonic parameters, the ultrasound waves transmitted by one group may be focused on one focal point, and the echoes of the ultrasound waves may be received simultaneously. Since the position of the focal point usually represents that the acoustic energy there may be relatively high and the amplitude of the received echoes there may be also relatively high, the brightness and the resolution of the image in the region around the focal point is usually higher than those of the image far away from the focal point. With application of the present disclosure to B imaging, the region around the focal point can be expanded along the direction of the depth to a certain extent, thereby improving the uniformity of the depth direction of B-mode images.

For those skilled in the art, it can be appreciated that all or part of the functions of the methods involved in the above-mentioned various embodiments may be implemented either by hardware or by computer programs. When all or parts of the functions in the above embodiments are realized by a computer program, such program may be stored in a computer-readable storage medium, which may include: read-only storage device, random storage device, magnetic disk, optical disk, hard disk, etc. The program may be executed by a computer to implement the aforesaid functions. For example, the program is stored in the storage device of the apparatus; and all or part of the above functions can be implemented when the program in the storage device is executed by a data processor. Moreover, when all or part of the functions involved in the above embodiments are implemented by a computer program, the program may also be stored in a storage medium (such as a server, another computer, a magnetic disk, an optical disk, a flash disk, or a mobile hard disk) and saved in the storage device of a local apparatus by downloading or copying or updated the version of the system of the local apparatus, so that the data processor may realize all or part of the functions above by executing the program stored in the storage device.

Specific examples have been described above to illustrate the present disclosure, which are only used to facilitate the understanding to the present disclosure, but not intended to limit the present disclosure. For those skilled in the art, several simple deductions, modifications or replacements may be made according to the concepts of the present disclosure.

The invention claimed is:

1. A method for detecting an elasticity with a shear wave, comprising:

transmitting ultrasound waves to a region of interest through transducers in an ultrasound probe that are configured to transmit ultrasound waves, wherein the ultrasound waves focus on at least two focus points in an acoustic field and drive a tissue so as to form a shear wave zone with shear wave sources corresponding to the at least two focus points that propagates in a direction perpendicular to a transmission direction of the ultrasound waves, and wherein the at least two focus points are disposed sequentially in the transmission direction of the ultrasound waves;

continuously transmitting detection ultrasound waves for a predetermined duration to a propagation path of the shear wave zone through transducers configured to transmit detection ultrasound waves, and receiving echo signals of the detection ultrasound waves; and calculating elastic characteristics based on the echo signals.

2. The method of claim 1, wherein the transducers are divided into at least two groups, wherein the ultrasound waves transmitted by one group are focused on one focus point.

3. The method of claim 2, further comprising: before the ultrasound waves are transmitted, outputting to the transducers parameters of the ultrasound waves to be transmitted for one time so as to divide the transducers into the at least two groups corresponding to their respective focus points.

4. The method according to claim 2, wherein each transducer of each group has a transmission delay based on a distance from said transducer to corresponding focus point, such that the ultrasound waves transmitted through transducers of each group arrive simultaneously at the focus point corresponding to said group.

5. The method of claim 4, wherein the ultrasound waves transmitted by different groups arrive simultaneously at corresponding focus points.

6. The method of claim 2, wherein a number of the transducers in each group is determined based on the following formula:

$$F\text{number} = \text{focus depth}/\text{transmitting aperture}$$

wherein, Fnumber is a characteristic value that represents a focus strength, focus depth is a distance from the focus point to a surface of the tissue, transmitting aperture is a width of the transducers that transmit the ultrasound waves to be focused on the focus point, and the width of the transducers is proportional to the number of the transducers.

7. The method of claim 1, wherein the at least two focus points are on a straight line or a curve in the acoustic field.

8. An ultrasound imaging method, comprising:

determining at least two focus points in a region of interest in a biological tissue, the at least two focus points being disposed sequentially along a direction in which ultrasound waves are transmitted;

outputting transmission parameters to transducers in an ultrasound probe that are configured to transmit the ultrasound waves, so as to divide the transducers into at least two groups, one group corresponding to one focus point;

transmitting ultrasound waves into the tissue through the transducers of each group according to the transmission parameters, so as to focus the ultrasound waves on the focus point corresponding to said group;

receiving echo signals of the ultrasound waves; and generating an ultrasound image according to the echo signals.

9. An ultrasound elasticity detecting apparatus, comprising an ultrasound probe, a transmitting/receiving controller and a data processor;

the ultrasound probe comprising a plurality of transducers configured to transmit ultrasound waves, the transducers being at least configured to transmit ultrasound waves to a region of interest that are focused on at least two focus points in an acoustic field, the ultrasound waves driving a tissue so as to form a shear wave zone with shear wave sources corresponding to the at least two focus points that propagates in a direction perpendicular to a transmission direction of the ultrasound waves; the ultrasound probe being further configured to continuously transmit detection ultrasound waves for a predetermined duration to a propagation path of the shear wave zone and receive echoes of the detection ultrasound waves, wherein the at least two focus points are disposed sequentially in the transmission direction of the ultrasound waves;

the transmitting/receiving controller being configured to generate transmission parameters and output the transmission parameters to the ultrasound probe, the transmission parameters comprising parameters of the ultrasound waves or parameters of the detection ultrasound waves; and the data processor being configured to calculate an elastic characteristic based on the echoes of the detection ultrasound waves.

10. The apparatus of claim 9, wherein the transducers are divided into at least two groups, one group corresponding to one focus point.

11. The apparatus of claim 10, wherein the transducers are divided into the at least two groups by the parameters of the ultrasound waves.

12. The apparatus of claim 10, wherein each transducer of each group has a transmission delay based on a distance from said transducer to corresponding focus point, such that the ultrasound waves transmitted through the transducers of each group arrive simultaneously at the focus point corresponding to said group.

13. The apparatus of claim 12, wherein the ultrasound waves transmitted by different groups arrive simultaneously at corresponding focus points.

14. The apparatus of claim 9, wherein a number of the transducers in each group is determined based on the following formula:

$$F\text{number} = \text{focus depth}/\text{transmitting aperture}$$

wherein, Fnumber is a characteristic value that represents a focus strength, focus depth is a distance from the focus point to a surface of the tissue, transmitting aperture is a width of the transducers that transmit the ultrasound waves focused on the focus point, and the width of the transducers is proportional to the number of the transducers.

15. The apparatus of claim 9, wherein the at least two focus points are on a straight line or a curve in the acoustic field.

16. The method of claim 8, wherein each transducer of each group has a transmission delay based on a distance from said transducer to corresponding focus point, such that the ultrasound waves transmitted through transducers of each group arrive simultaneously at the focus point corresponding to said group.

17. The method of claim 8, wherein the ultrasound waves transmitted by different groups arrive simultaneously at corresponding focus points.

* * * * *